US007172630B2

(12) United States Patent
Christensen

(10) Patent No.: US 7,172,630 B2
(45) Date of Patent: Feb. 6, 2007

(54) PROSTHETIC FOOT WITH CAM

(75) Inventor: Roland J. Christensen, Fayette, UT (US)

(73) Assignee: Roland J. Christensen, as operating Manager of RJC Development, LC, General Partner of the Roland J. Christensen Family Limited Partnership, Gunnison, UT (US)

( * ) Notice: Subject to any disclaimer, the term of this patent is extended or adjusted under 35 U.S.C. 154(b) by 207 days.

(21) Appl. No.: 10/783,559

(22) Filed: Feb. 20, 2004

(65) Prior Publication Data

US 2005/0187640 A1 Aug. 25, 2005

(51) Int. Cl.
A61F 2/66 (2006.01)
A61F 2/68 (2006.01)

(52) U.S. Cl. ...................................................... 623/53
(58) Field of Classification Search ............. 623/47–56
See application file for complete search history.

(56) References Cited

U.S. PATENT DOCUMENTS

| 42,799 | A | 5/1864 | Shepard |
| 92,031 | A | 6/1869 | Foster |
| 292,800 | A | 2/1884 | Furrer |
| 497,026 | A | 5/1893 | Judson |
| 1,001,641 | A | 8/1911 | Harrison |
| 1,289,580 | A | 12/1918 | Vincenti |
| 1,779,765 | A | 10/1930 | Eichhorn |
| 1,996,874 | A | 4/1935 | Mascau |
| 2,036,830 | A | 4/1936 | Rowley |
| 2,379,538 | A | 7/1945 | Meierhofer |
| 2,443,356 | A | 6/1948 | Mathis |
| 2,453,969 | A | 11/1948 | Carter |
| 2,470,480 | A | 5/1949 | Fogg |
| 2,570,735 | A | 10/1951 | Weise |
| 2,617,115 | A | 11/1952 | Ellery |
| 2,640,200 | A | 6/1953 | Wisburn |
| 2,843,853 | A | 7/1958 | Mauch |
| 3,551,914 | A | 1/1971 | Woodall |
| 3,754,286 | A | 8/1973 | Ryan |
| 3,871,032 | A | 3/1975 | Karas |
| 3,874,004 | A | 4/1975 | May |
| 3,906,552 | A | 9/1975 | Weber |

(Continued)

FOREIGN PATENT DOCUMENTS

DE 295807 12/1916

(Continued)

Primary Examiner—Alvin J. Stewart
(74) Attorney, Agent, or Firm—Thorpe North & Western

(57) ABSTRACT

A prosthetic foot device includes an elongated continuous cantilever-spring, extending from an attachment section coupleable to a stump of an amputee to a toe section at a toe location of a natural foot. The cantilever-spring is elastically deformable under a load to store energy as the amputee steps onto the cantilever-spring and to release energy as the amputee steps off of the cantilever-spring. A cam is pivotally coupled to the cantilever-spring at a pivot. A resistance arm is coupleable to the stump of the amputee, and extends to a displaceable section engaging the cam. A lever arm is attached to the cantilever-spring and engages the cam. The cam operatively inter-couples the cantilever-spring and the resistance arm to elastically deform the resistance arm along with the cantilever-spring to collectively store more energy than the cantilever-spring alone.

18 Claims, 8 Drawing Sheets

U.S. PATENT DOCUMENTS

| | | | |
|---|---|---|---|
| 3,920,610 A | 11/1975 | Wagner | |
| 3,956,775 A | 5/1976 | Moore | |
| 3,982,280 A | 9/1976 | Asbelle et al. | |
| 4,089,072 A | 5/1978 | Glabiszewski | |
| 4,328,594 A | 5/1982 | Campbell et al. | |
| 4,442,554 A | 4/1984 | Copes | |
| 4,506,395 A | 3/1985 | Haupt | |
| 4,547,913 A | 10/1985 | Phillips | |
| 4,636,220 A | 1/1987 | Ziegelmeyer | |
| 4,645,509 A | 2/1987 | Poggi et al. | |
| 4,676,801 A | 6/1987 | Lundeen | |
| 4,721,510 A | 1/1988 | Cooper et al. | |
| 4,822,363 A | 4/1989 | Phillips | |
| 4,865,611 A | 9/1989 | Al-Turaiki | |
| 4,938,775 A | 7/1990 | Morgan | |
| 4,959,073 A | 9/1990 | Merlette | |
| 5,019,109 A | 5/1991 | Voisin | |
| 5,030,239 A | 7/1991 | Copes | |
| 5,037,444 A | 8/1991 | Phillips | |
| 5,112,356 A | 5/1992 | Harris et al. | |
| 5,116,383 A | 5/1992 | Shorter et al. | |
| 5,116,384 A | 5/1992 | Wilson et al. | |
| 5,156,632 A | 10/1992 | Wellershaus | |
| 5,181,932 A | 1/1993 | Phillips | |
| 5,181,933 A | 1/1993 | Phillips | |
| 5,217,500 A | 6/1993 | Phillips | |
| 5,219,365 A | 6/1993 | Sabolich | |
| 5,290,319 A | 3/1994 | Phillips | |
| 5,314,499 A | 5/1994 | Collier, Jr. | |
| 5,376,133 A | 12/1994 | Gramnas | |
| 5,376,139 A | 12/1994 | Pitkin | |
| 5,376,141 A | 12/1994 | Phillips | |
| 5,387,246 A | 2/1995 | Phillips | |
| 5,425,781 A | 6/1995 | Allard et al. | |
| 5,425,782 A | 6/1995 | Phillips | |
| 5,443,528 A | 8/1995 | Allen | |
| 5,443,529 A | 8/1995 | Phillips | |
| 5,458,656 A | 10/1995 | Phillips | |
| 5,464,441 A | 11/1995 | Phillips | |
| 5,482,513 A | 1/1996 | Wilson | |
| 5,486,209 A | 1/1996 | Phillips | |
| 5,507,838 A | 4/1996 | Chen | |
| 5,509,936 A | 4/1996 | Rappoport et al. | |
| 5,509,938 A | 4/1996 | Phillips | |
| 5,514,185 A | 5/1996 | Phillips | |
| 5,514,186 A | 5/1996 | Phillips | |
| 5,549,714 A | 8/1996 | Phillips | |
| 5,571,210 A | 11/1996 | Lindh | |
| 5,571,213 A | 11/1996 | Allen | |
| 5,593,455 A | 1/1997 | Phillips | |
| 5,593,456 A | 1/1997 | Merlette | |
| 5,593,457 A | 1/1997 | Phillips | |
| 5,653,767 A | 8/1997 | Allen et al. | |
| 5,725,598 A | 3/1998 | Phillips | |
| 5,728,175 A | 3/1998 | Rincoe | |
| 5,728,176 A | 3/1998 | Phillips | |
| 5,728,177 A | 3/1998 | Phillips | |
| 5,766,265 A | 6/1998 | Phillips | |
| 5,769,896 A | 6/1998 | Rosendahl et al. | |
| 5,776,205 A | 7/1998 | Phillips | |
| 5,779,735 A | 7/1998 | Molino | |
| 5,800,564 A | 9/1998 | Gelineau | |
| 5,800,565 A | 9/1998 | Biedermann | |
| 5,800,569 A | 9/1998 | Phillips | |
| 5,824,112 A | 10/1998 | Phillips | |
| 5,888,238 A | 3/1999 | Phillips et al. | |
| 5,893,891 A | 4/1999 | Zahedi | |
| 5,899,944 A * | 5/1999 | Phillips | 623/55 |
| 5,913,902 A | 6/1999 | Geible | |
| 5,944,760 A * | 8/1999 | Christensen | 623/55 |
| 5,957,981 A | 9/1999 | Gramnas | |
| 5,976,191 A | 11/1999 | Phillips | |
| 5,993,488 A | 11/1999 | Phillips | |
| 6,019,795 A | 2/2000 | Phillips | |
| 6,071,313 A | 6/2000 | Phillips | |
| 6,120,547 A | 9/2000 | Christensen | |
| 6,165,227 A | 12/2000 | Phillips | |
| 6,187,052 B1 | 2/2001 | Molino et al. | |
| 6,197,068 B1 | 3/2001 | Christensen | |
| 6,206,934 B1 | 3/2001 | Phillips | |
| 6,228,124 B1 | 5/2001 | Slemker et al. | |
| 6,241,776 B1 * | 6/2001 | Christensen | 623/52 |
| 6,254,643 B1 | 7/2001 | Phillips | |
| 6,261,324 B1 | 7/2001 | Merlette | |
| 6,280,479 B1 * | 8/2001 | Phillips | 623/62 |
| 6,290,730 B1 | 9/2001 | Pitkin et al. | |
| 6,306,178 B1 * | 10/2001 | Kania et al. | 623/52 |
| 6,402,790 B1 | 6/2002 | Celebi | |
| 6,663,673 B2 * | 12/2003 | Christensen | 623/56 |
| 6,875,241 B2 * | 4/2005 | Christesen | 623/56 |
| 2002/0133237 A1 | 9/2002 | Christensen | |

FOREIGN PATENT DOCUMENTS

| | | |
|---|---|---|
| GB | 1191633 | 5/1970 |
| GB | 1550658 | 11/1976 |
| IT | 556381 | 2/1957 |
| RU | 2033772 | 4/1995 |

* cited by examiner

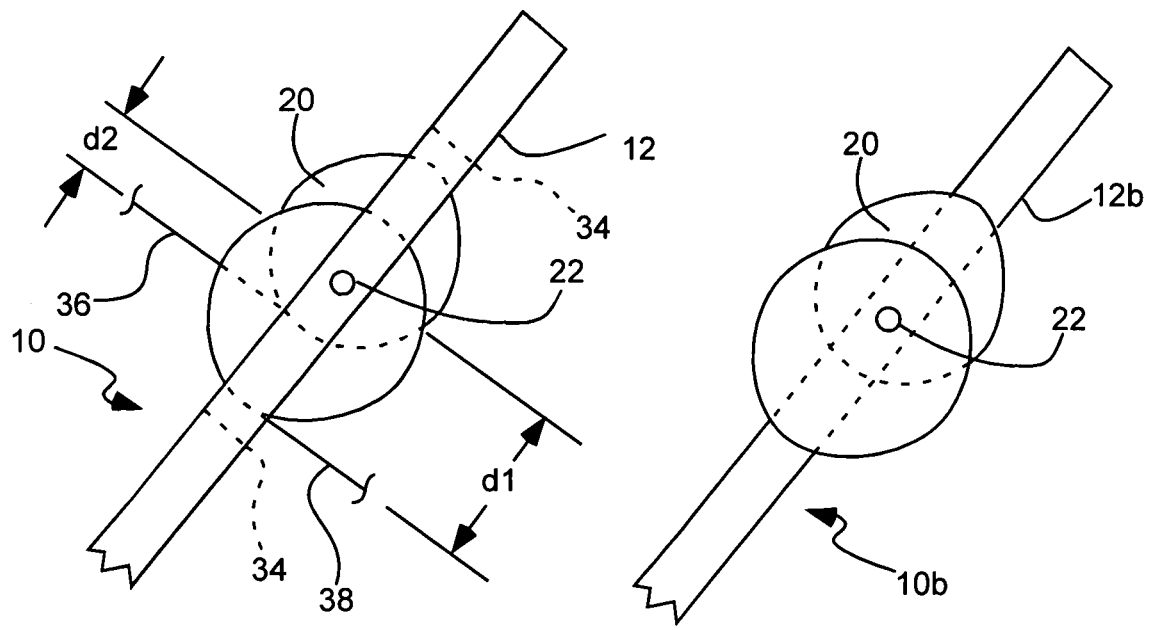
FIG. 2b
FIG. 2c
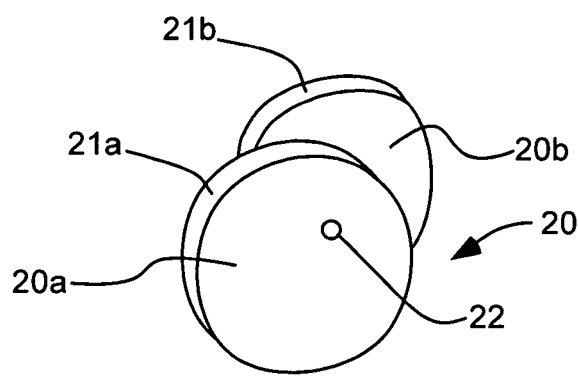
FIG. 2a

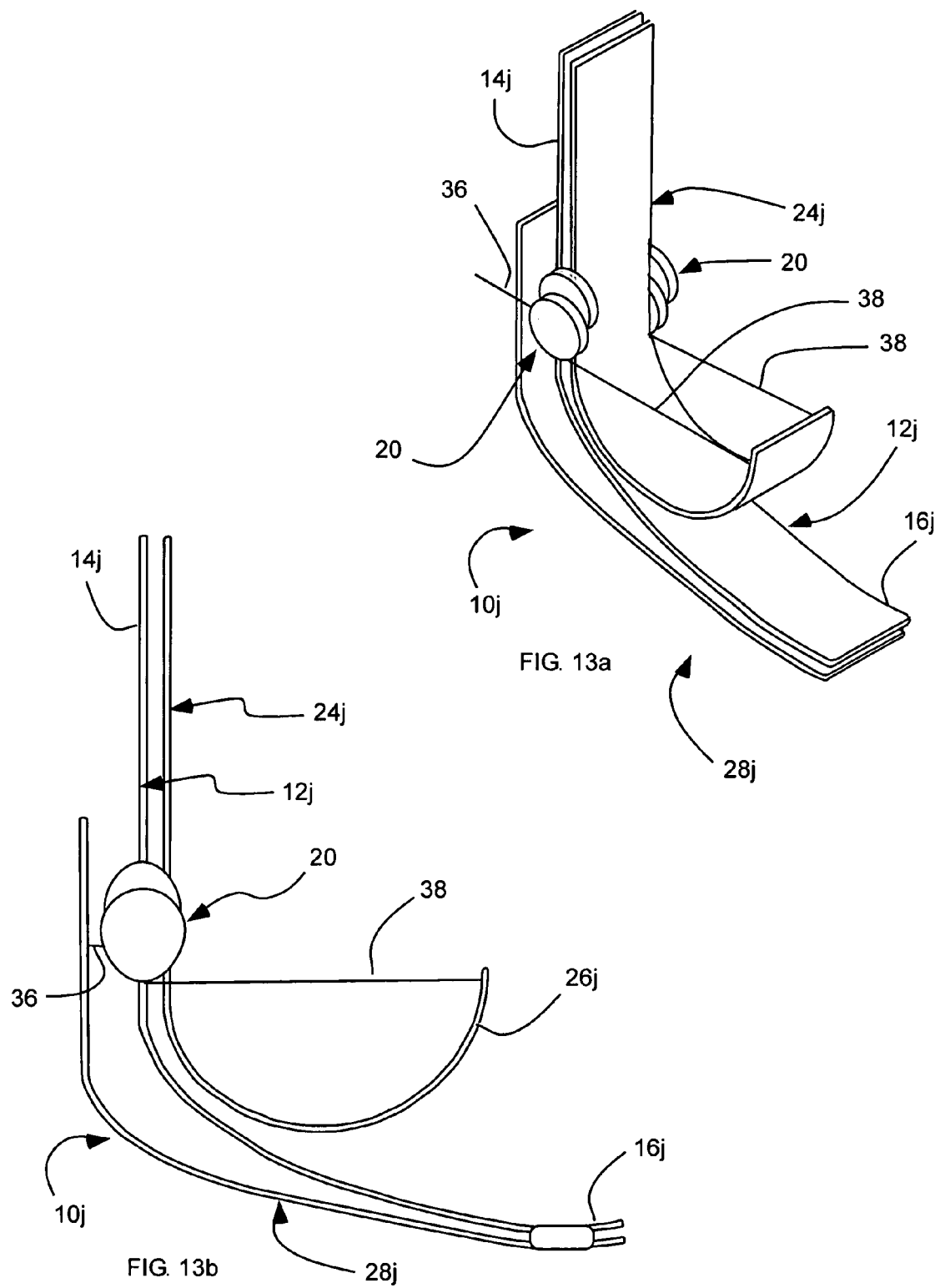

PROSTHETIC FOOT WITH CAM

BACKGROUND OF THE INVENTION

1. Field of the Invention

The present invention relates generally to prosthetic feet. More particularly, the present invention relates to a prosthetic foot with a plurality of cantilever-springs inter-coupled to have a non-linear force versus deflection relationship and to store more energy together than alone.

2. Related Art

Many individuals have lost a limb for various reasons such as war, accident, or disease. In most instances these individuals are not only able to live relatively normal lives, but are able to lead physically active lives as well. Oftentimes, these individuals are aided in their everyday lives by a prosthetic limb. Prosthetic limbs, or prosthesis, generally provide an artificial limb that simulates the function and natural feel of the lost limb.

With respect to prosthetic feet, the development of functional and natural artificial feet has been pursued for some time. Many designs have attempted to copy the anatomy of the foot, or simulate its natural action, by replacing the bones and muscle with various mechanical components. Other designs have departed radically from mere anatomical copying or mechanical simulation of a natural foot by replacing the entire foot with an energy storage element, such as a spring. In this type of design, as the user steps onto the foot, the user's weight compresses the spring. As the user moves forward, the user's weight comes off the foot and the energy stored in the spring is used to propel the user forward.

In addition to the basic use of a spring in a prosthetic foot, it has been attempted to alter the performance of these energy storing feet in a variety of ways: such as by using multiple springs in various configurations; using bladders or materials disposed between various elements of the foot; and using multiple springs that deflect at different intervals of foot deflection to add resistance.

While each of these variations has added some benefit to the field of energy storing prosthetic feet, they have often met with limitations introduced by the general nature of springs. This is due to the fact that the force stored by springs is often linearly proportional to the distance over which the spring has been stretched or compressed. That is, a unit of displacement of the spring generally results in a substantially constant multiple of the unit of displacement being stored in the spring. Thus, typical prosthetic feet utilizing springs have been limited to storage of energy in the spring in an amount that corresponds to a constant multiple of the distance over which the spring was compressed or stretched. This has resulted in a limited amount of energy being storable in the spring and does not effectively leverage the energy expended by a user of the prosthetic foot.

SUMMARY OF THE INVENTION

It has been recognized that it would be advantageous to develop a prosthetic foot that enables energy storage within, and release from, the foot in a nonlinear, maximized manner.

The invention provides a prosthetic foot device, including an elongated continuous cantilever-spring, extending from an attachment section coupleable to a stump of an amputee to a toe section at a toe location of a natural foot. The cantilever-spring can be elastically deformable under a load to store energy as the amputee steps onto the cantilever-spring and to release energy as the amputee steps off of the cantilever-spring. A cam can be pivotally coupled to the cantilever-spring at a pivot. A resistance arm can be coupleable to the stump of the amputee, and can extend to a displaceable section engaging the cam. A lever arm can be attached to the cantilever-spring and can engage the cam. The cam can operatively inter-couple the cantilever-spring and the resistance arm to elastically deform the resistance arm along with the cantilever-spring to collectively store more energy than the cantilever-spring alone.

In addition, the invention provides a prosthetic foot device, including a plurality of cantilever-springs being capable of elastic deformation under a load to store and release energy. A cam can be pivotal with respect to the cantilever-springs, the cam operatively inter-coupling the cantilever-springs such that the cantilever-springs store more energy together than alone. One of the cantilever-springs can have an attachment section coupleable to a stump of an amputee and can define a unitary foot member extending continuously from the attachment section to a toe section at a toe location of a natural foot.

Furthermore, the invention provides a prosthetic foot device, including a plurality of cantilever-springs, each having an attachment section coupleable to a stump of an amputee. The cantilever-springs can be capable of elastic deformation under a load to store and release energy. One of the cantilever-springs can define a unitary foot member extending continuously from the attachment section to a toe section at a toe location of a natural foot. Means for variably inter-coupling the cantilever-springs can be provided so that one of the cantilever-springs applies a varying resistance force to the foot member that varies as the foot member deflects.

Additional features and advantages of the invention will be apparent from the detailed description which follows, taken in conjunction with the accompanying drawings, which together illustrate, by way of example, features of the invention.

BRIEF DESCRIPTION OF THE DRAWINGS

FIG. 1b is a side view of the prosthetic foot of FIG. 1a;

FIG. 1c is schematic view of a graph of force vs. deflection of the prosthetic foot of FIG 1a;

FIG. 2a is perspective view of a cam of the prosthetic foot of FIG. 1a;

FIG. 2b is a partial side view of a cantilever-spring and cam of the prosthetic foot of FIG. 1a;

FIG. 2c is a partial side view of another embodiment of a cantilever-spring and cam in accordance with an embodiment of the present invention;

FIG. 13a is a perspective view of another prosthetic foot in accordance with an embodiment of the present invention; and FIG. 13b is a side view of the prosthetic foot of FIG. 13a.

DETAILED DESCRIPTION

Figure 1A:
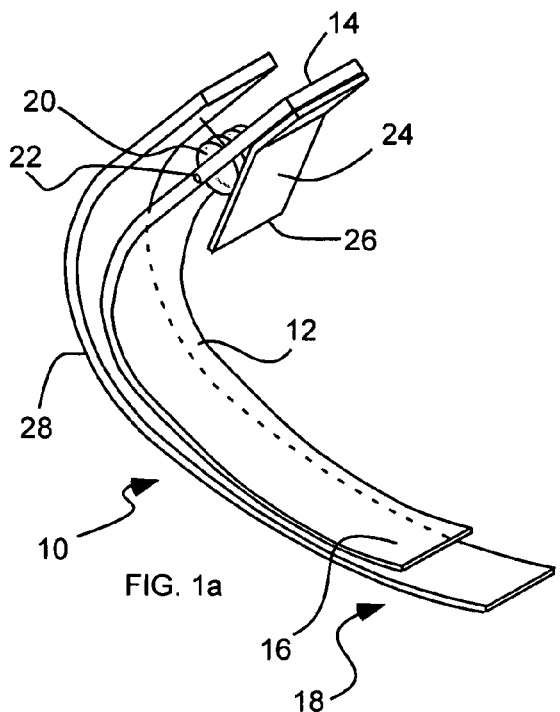
FIG. 1a is a perspective view of a prosthetic foot in accordance with an embodiment of the present invention.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

Figure 1C:
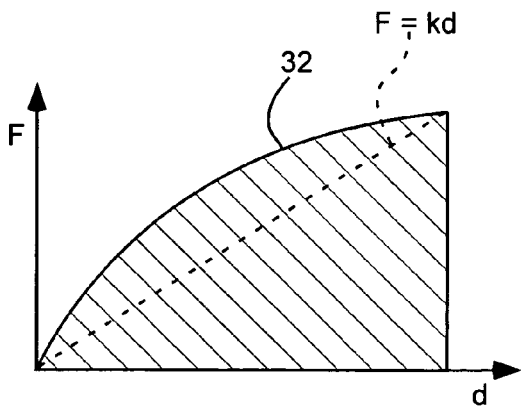
Figure 1B:
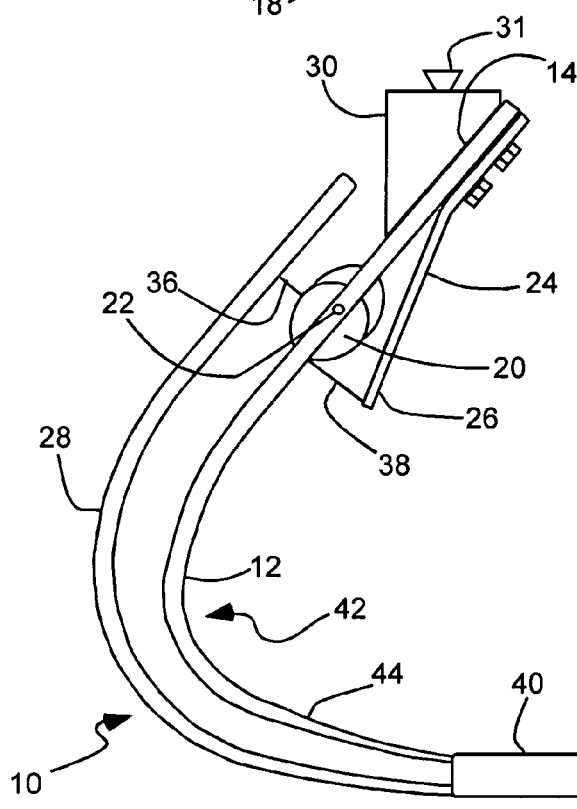

As illustrated in FIGS. 1a and 1b, a prosthetic foot or prosthetic foot device, indicated generally at 10, in accordance with the present invention is shown for use with an amputee. The prosthetic foot 10 can include a plurality of cantilever-springs that elastically deform under a load to store and release energy, and that are operatively inter-coupled to have a non-linear force versus deflection relationship, as shown in FIG. 1c, and to collectively store more energy together than alone, represented by the area under the curve in FIG. 1c. As discussed in greater detail below, the prosthetic foot can include a cam operatively inter-coupling the cantilever-springs.

One of the plurality of cantilever-springs can include an elongated continuous cantilever-spring 12 defining a unitary foot member. The cantilever-spring 12 or foot member includes an attachment section 14 that is couplable to a stump or socket (not shown) of an amputee. The stump of the amputee can be received in the socket, which can have a standard attachment for the prosthetic foot, as is known in the art. The cantilever-spring 12 or foot member can extend from the attachment section 14 to a toe section 16 at a toe location 18 of a natural foot (not shown). In addition, the foot member can extend through an ankle section and an arch section. The foot member can form a substantial arc with a general c-shape. The cantilever-spring 12 can be elastically deformable under a load to store energy as the amputee steps onto the cantilever-spring, and to release energy as the amputee steps off of the cantilever-spring. As described in greater detail below, the prosthetic foot can also include a cam 20 pivotally coupled to the cantilever-spring 12 at a pivot 22.

Another of the plurality of cantilever-springs can include a resistance arm 24 with an attachment section couplable to the stump of the amputee and extendable to a displaceable section 26. The attachment section of the resistance arm 24 can be coupled at the attachment section of the cantilever-spring 12 or foot member. The displaceable section 26 can engage the cam 20, as discussed below.

A lever arm 28 can be attached to the cantilever-spring 12 or foot member. The lever arm 28 can form a substantial arc with a general c-shape, similar to the foot member. The lever arm 28 can partially extend around the cantilever-spring 12 or foot member. A bottom portion or attachment section of the lever arm 28 can be attached to the cantilever-spring 12 or foot member, such as underneath the foot member at the arch section or near the toe section. In addition, the lever arm 28 can extend to an upper end or displaceable section that can engage the cam 20, as discussed below. Thus, the cam operatively inter-couples the cantilever-spring 12 and the resistance arm 24 to elastically deform the resistance arm 24 along with the cantilever-spring 12 to collectively store more energy than the cantilever-spring alone.

The prosthetic foot can be utilized by a variety of amputees having various stump configurations. The prosthetic foot can be attached to a stump or socket through a variety of manners known to those skilled in the art. One such exemplary attachment configuration is shown in FIG. 1b, where an attachment member 30 is shown coupled to the attachment section 14 of cantilever-spring 12, and to the attachment section of the resistance arm 24. An attachment device 31 can be used to inter-couple the attachment member 30 to the stump or socket (not shown) of the amputee. The attachment device 31 can be of a variety of configurations known to those in the art, including the inverted frusto-pyramidal shape shown in FIG. 1b. As the user of the prosthetic "steps onto" the cantilever-spring, the spring is compressed and, in cooperation with the various cantilever-springs, cams and resistance arms (discussed in more detail herein), absorbs energy correlating to the user's weight disposed on the spring. As the user removes weight from the spring by "stepping off" the prosthetic foot, the energy stored by the spring is released to aid in propelling the user forward.

The present invention thus advantageously combines a cantilever-spring with various cams, lever arms and resistance arms to collectively store more energy than would be stored by use of the cantilever-spring alone. As illustrated by example in FIG. 1c, the force produced by a conventional spring is generally linear, as represented by line F=kd, "F" representing force, "k" representing a spring constant, and "d" representing the distance over which the spring is deflected. Thus, a conventional foot prosthetic utilizing a conventional spring has a substantially linear force versus deflection relationship, indicated by the dashed line. In contrast, the inter-coupled cantilever-springs of the present prosthetic foot in non-linear, indicated by the solid line 32. The energy stored by the present prosthetic foot, shown by the shaded area under the curve, is greater than a conventional spring. In this manner the present invention provides increased force in propelling a user forward as the user steps off the prosthetic foot.

As shown in greater detail in FIG. 1b, the cam 20 can be carried by the cantilever-spring 12 in a notch or aperture (the edges of which are shown by example in hidden view at 34 in FIG. 2b). The cam can be pivotally coupled within the cantilever-spring by pivot 22. The lever arm 28 can engage the cam via a cable or chord 36, which can be a variety of chord or cable types known to those in the art, and can be formed of a variety of materials, including metals, polymers, natural fibers, etc. The resistance arm 24 can engage the cam 20 via a chord 38 attached to displaceable section 26. Alternatively, a prosthetic foot 10b can have the cam 20 disposed on a side of the cantilever-spring 12b, as shown in FIG. 2c.

The cantilever-spring 12 and the lever arm 28 can be coupled by a connector 40 shown in FIG. 1b. The connector 40 can include a wrap of resin impregnated fiber. In addition, the cantilever-spring 12 or foot member can be curvilinear and can extend continuously from the attachment section 14, through an ankle section 42 and an arch section 44, to the toe section 16. The plurality of cantilever springs, including the cantilever-spring 12 or foot member and the resilient arm 24, can be formed of a composite material, such as a resin impregnated fiber. The fiber can include a graphite fiber, and can be provided in a fiber mat. Similarly, the lever arm also can be formed of a composite material, and can also form a cantilever-spring.

Figure 3A:
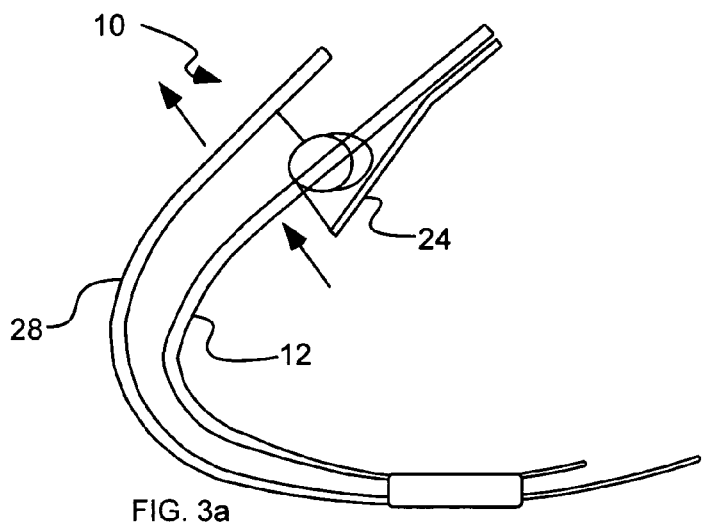
FIGS. 3a, 4a and 5a are side views of the prosthetic foot of FIG. 1a shown in varying degrees of deflection.
Figure 4A:
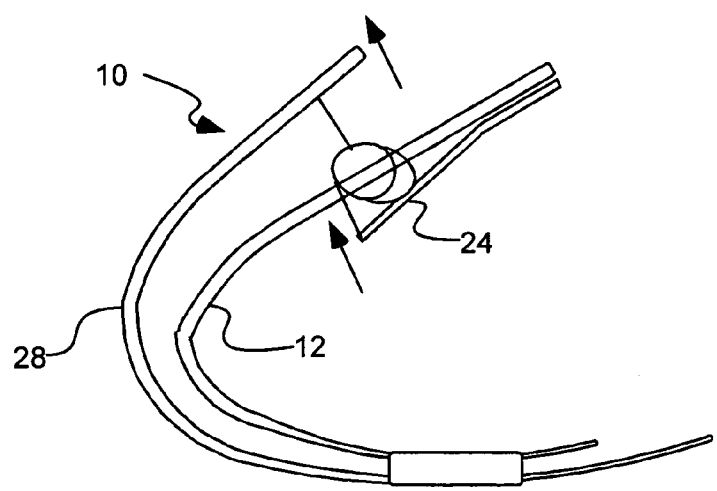
Figure 5A:
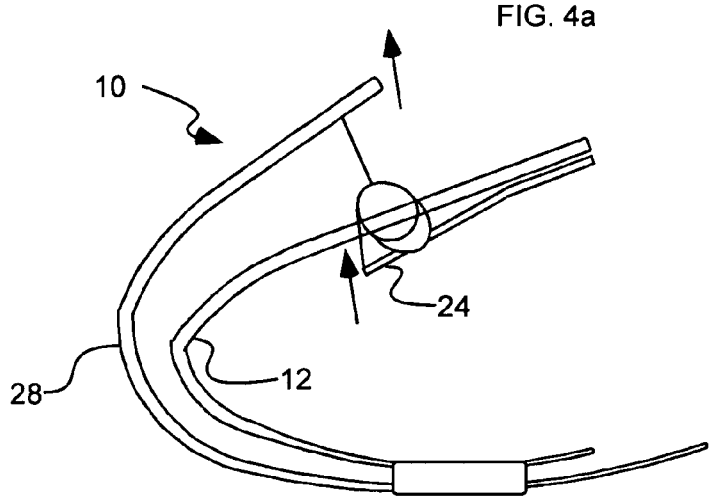

Referring to FIGS. 3a, 4a and 5a, the prosthetic foot 10 is shown schematically in varying degrees of deflection. The prosthetic foot is shown in FIG. 3a in one exemplary beginning position. As a user applies weight to the cantilever-spring 12 the cantilever-spring deflects inwardly, or the attachment section deflect downwardly. The lever arm 28 resists deflection, and pulls on the cam 20 via the cable 36. Thus, the cam 20 pivots about pivot 22 as the lever arm 28 resists deflection and pulls on the cam. As the cam 20 pivots, the can pulls on the resistance arm 24 via the cable 38, causing the resistance arm to deflect generally towards the cantilever-spring 12. This continued series of movement in response to deflection of cantilever-spring 12 is shown in incrementally greater degrees in FIGS. 3a, 4a and 5a. The movement of the cam 20 is shown in greater detail in FIGS. 3b, 4b and 5b, which correspond generally to FIGS. 3a, 4a and 5a, but are shown in a different (vertical) orientation for clarity.

Referring to FIG. 2b, the lever arm 28 and the resistance arm 24 can initially engage the cam, via chords 36 and 38, at different distances from the pivot 22. The lever arm 28 can engage the cam 20 at a closer distance d2 to the pivot 22, and the resistance arm 24 can engage the cam at a further distance d1 to the pivot. By engaging the lever arm and resistance arm at different distances from the pivot, the prosthetic foot can be configured to increase or decrease the initial force applied by the cam to the resistance arm in order to increase or decrease the energy stored by the respective arm.

Figure 3B:
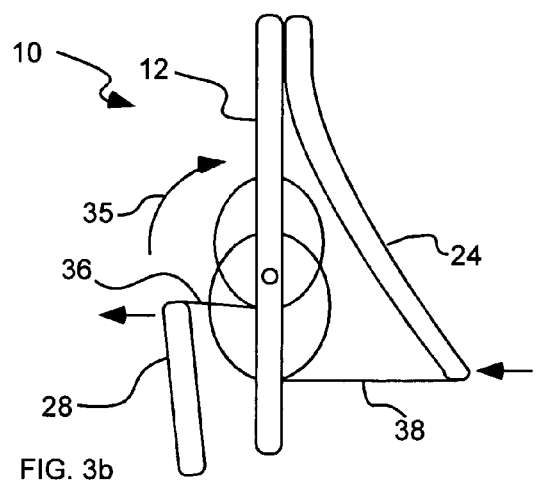
FIGS. 3b, 4b and 5b are partial side schematic views of the prosthetic foot of FIG. 1a shown in varying degrees of deflection.
Figure 4B:
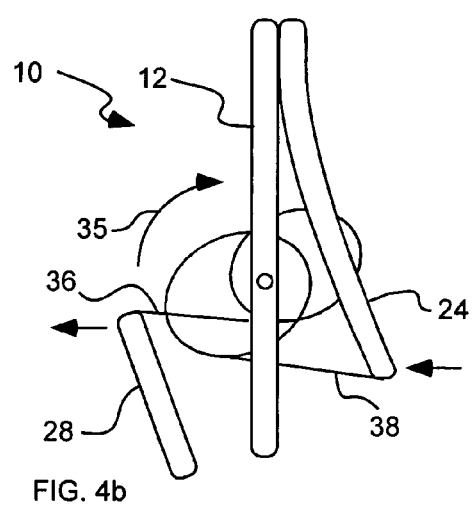
Figure 5B:
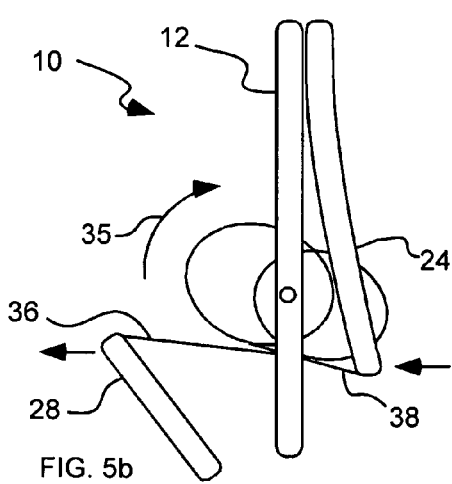

As shown in more detail in FIGS. 3b, 4b and 5b, the resistance arm 24 and the lever arm 28 can engage the cam 20 at varying distances from the pivot 22 as the cam pivots, indicated by arrow 35. The lever arm 28 can engage the cam 20 at a distance varying from closer to further as the cam pivots. The resistance arm 24 can engage the cam 20 at a distance varying from further to closer as the cam pivots. This relationship can be appreciated in the views of FIGS. 3b through 5b, which illustrate progressive movement of the resistance arm and lever arm toward and away from the cantilever-spring, respectively, as the cantilever beam is subject to deflection (for ease of understanding, the cantilever-spring is shown in FIGS. 3b, 4b and 5b in a substantially vertical orientation, it being understood that the cantilever-spring will generally deflect in a downward orientation during use). Also, while not so limited, the lever arm and the resistance arm can be disposed on opposite sides of the cantilever-spring.

As illustrated in FIG. 2a, the cam 20 includes a pair of lobes 20a and 20b disposed at different circumferential positions with respect to the pivot 22. In this manner, a differing degree of deflection of can be provided to each of the resistance arm 24 and the lever arm 28 (neither shown in FIG. 2a). In another aspect, the cam 20 can include a dual cam with a pair of lobes 20a and 20b disposed at different circumferential positions with respect to the pivot 22. In another aspect, the cam 20 can include a pair of cams 20a and 20b fixed to one another and pivotal together, the pair of cams being oriented at different orientations with respect to one another. The cam 20, or cams 20a and 20b, can have a pair of tracks 21a and 21b that can extend around at least a portion of a perimeter of the one or more cams. The tracks can thus extend at different circumferential distances from the pivot 22.

Figure 6A:
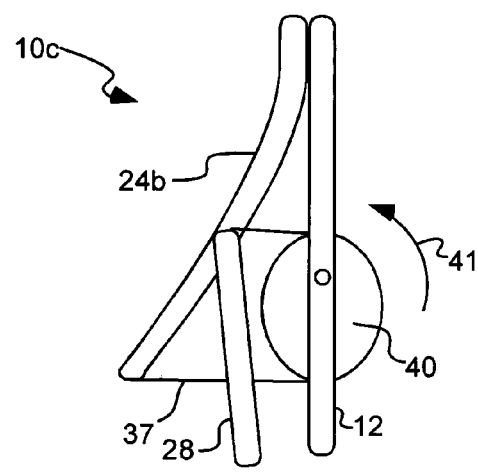
FIGS. 6a, 6b and 6c are partial side schematic views of another prosthetic foot in accordance with another embodiment of the present invention, shown in varying degrees of deflection.
Figure 6B:
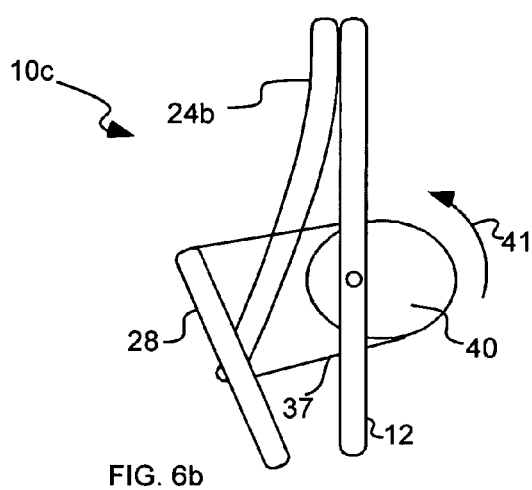
Figure 6C:
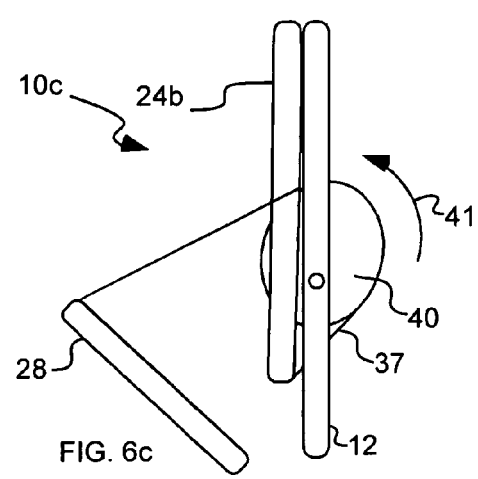

While some aspects of the invention include a cam with two lobes, or a pair of offset cams, it is to be understood that the present invention is not so limited. For example, as shown in FIGS. 6a through 6c, a prosthetic foot 10c can include a single cam 40 operatively inter-coupling the resistance arm 24b with the lever arm 28, and thus the cantilever-spring 12. In this aspect of the invention, the resistance arm and lever arm can be disposed on the same side of the cantilever-spring 12. Thus, as the cantilever-spring deflects in response to weight applied to the foot, the cam rotates about the pivot, indicated by arrow 41, causing the resistance arm to move toward the cantilever-spring as the lever arm moves away from the cantilever-spring. In this embodiment, a common chord or cable 37 can inter-couple the resistance arm and the lever arm.

Figure 7:
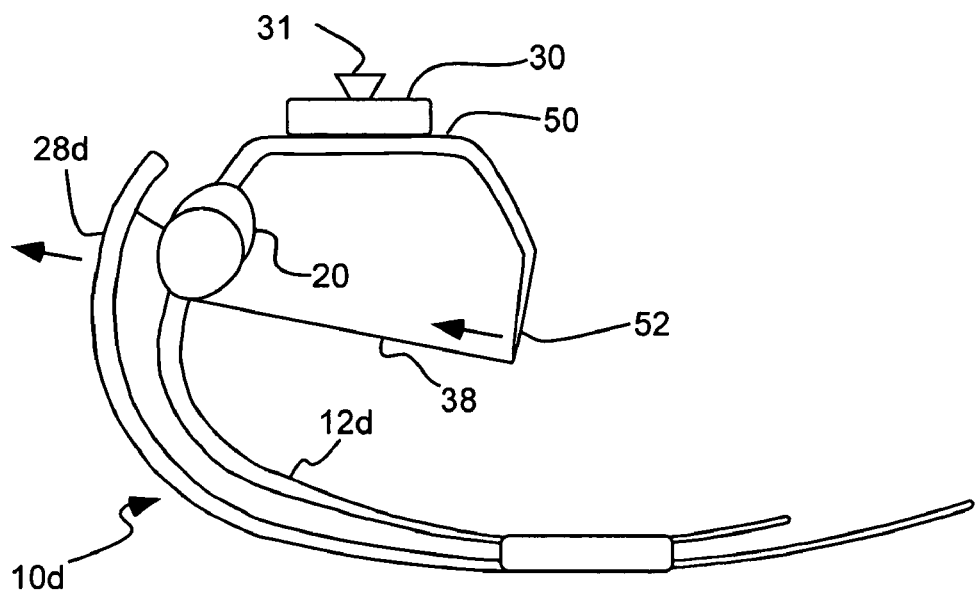
FIG. 7 is a side view of another prosthetic foot in accordance with the present invention.

Referring to FIG. 7, another prosthetic foot 10b is shown that is similar in many respects to that described above. A cantilever-spring 12d can include an upper support section or attachment section 50 onto which the stump attachment member 30 can be disposed. The cantilever-spring can include an integral and continuous resistance section 52 which can engage the cam 20 via a chord 38. This embodiment is similar to the embodiments discussed above in that the displacement section 52 deflects toward the cantilever-spring 12d as the cantilever-spring deflects. Similarly, a lever arm 28d can engage the cam and can deflect away from the cantilever-spring as the cantilever-spring deflects.

The cams, or the cams and the lever arms, described above are examples of a means for variably inter-coupling the cantilever-springs so that one of the cantilever-springs applies a varying resistance force to the foot member that varies as the foot member deflects. Other means can be used, examples of which are described below.

Figure 8:
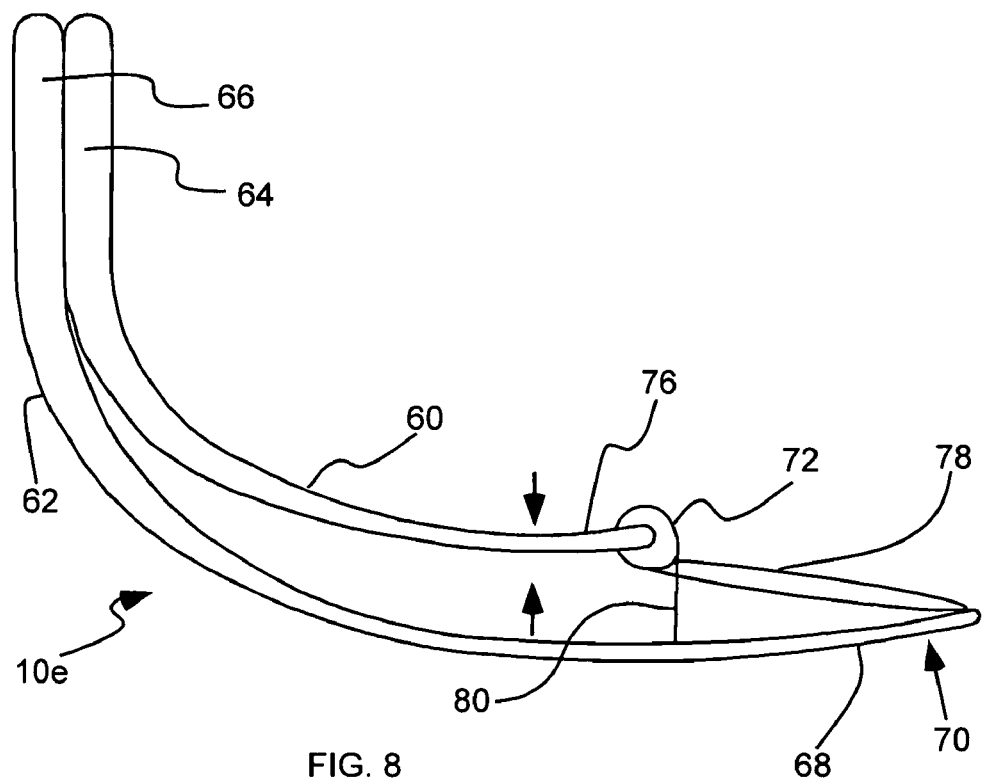
FIG. 8 is a side view of another prosthetic foot in accordance with the present invention.

Referring to FIGS. 8–12, various different prosthetic feet are illustrated that are similar in many respects to those described above. These prosthetic feet can employ many of the features and advantages of above described feet, including dual-lobed and/or tracked cams, curvilinear cantilever-springs, etc. Referring to FIG. 8, a prosthetic foot 10e includes a plurality of cantilever-springs 60 and 62, each having an attachment section 64 and 66, respectively, couplable to a stump or socket of an amputee (not shown). The cantilever-springs can each be capable of elastic deformation under a load to store and release energy. One of the cantilever-springs 62 can define a unitary foot member extending continuously from the attachment section 66 to a toe section 68 at a toe location 70 of a natural foot. Another of the cantilever-springs can define a resistance arm 60 with a deflection section 76. The prosthetic foot can include means for variably inter-coupling the cantilever-springs so that one of the cantilever-springs applies a varying resistance force to the foot member that varies as the foot member deflects.

The means for variably inter-coupling the cantilever-springs can include a cam 72 pivotally coupled to the deflection section 76 of the resistance arm 60. A lever arm 78 can be fixedly attached to the cam 72 and can engage the foot member 62. A chord or cable 80 can be coupled to the cam and can engage the foot member. As the foot member 60 deflects, it displaces the lever arm 78. As the lever arm displaces, it pivots the cam 72. As the cam 72 pivots, it pulls the cable 80, and thus pulls the foot member and the resistance arm together. In this manner, the cantilever-springs 60 and 62 are inter-coupled.

Figure 9:
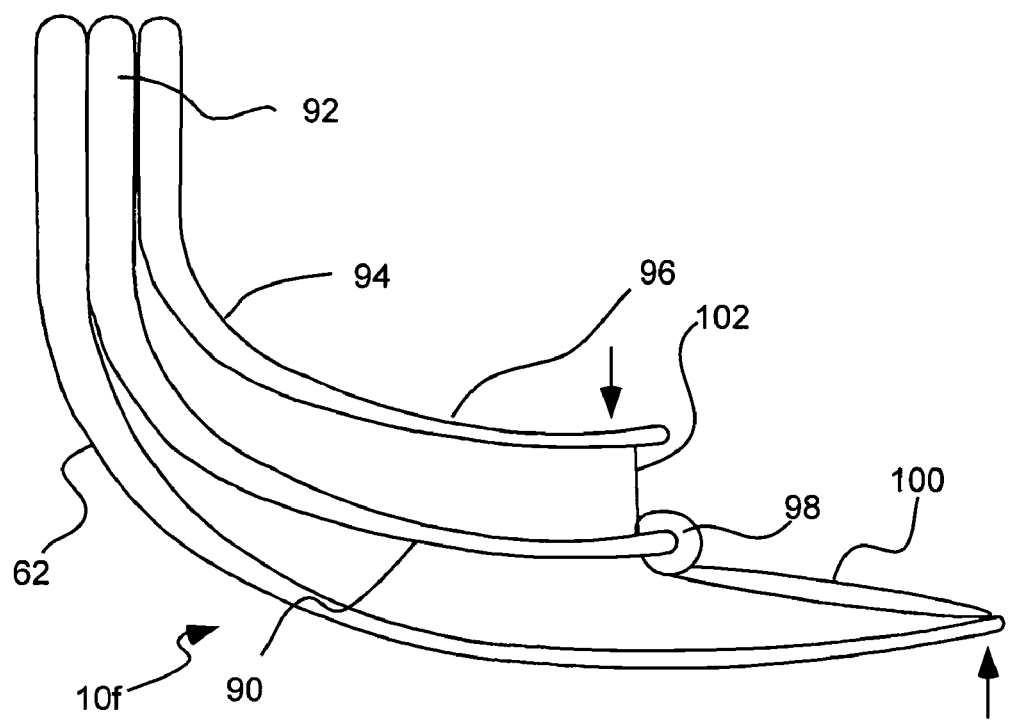
FIG. 9 is a side view of another prosthetic foot in accordance with the present invention.

Referring to FIG. 9, another prosthetic foot 10f includes a mounting arm 90 with an attachment section 92 coupleable to the stump or socket of the amputee (not shown). A cantilever-spring can define a resistance arm 94 with a deflection section 96. The means for variably inter-coupling the cantilever-springs can include a cam 98 pivotally coupled to the mounting arm 90. A lever arm 100 can be fixedly attached to the cam 98 and can engage the foot member 62. A chord or cable 102 can be coupled to the cam 98 and can engage the resistance arm 94. As the foot member 62 deflects, it displaces the lever arm 100. As the lever arm 100 displaces, it pivots the cam 98. As the cam 98 pivots, it pulls the cable 102, and thus pulls the foot member 62 and the resistance arm 94 together.

Figure 10:
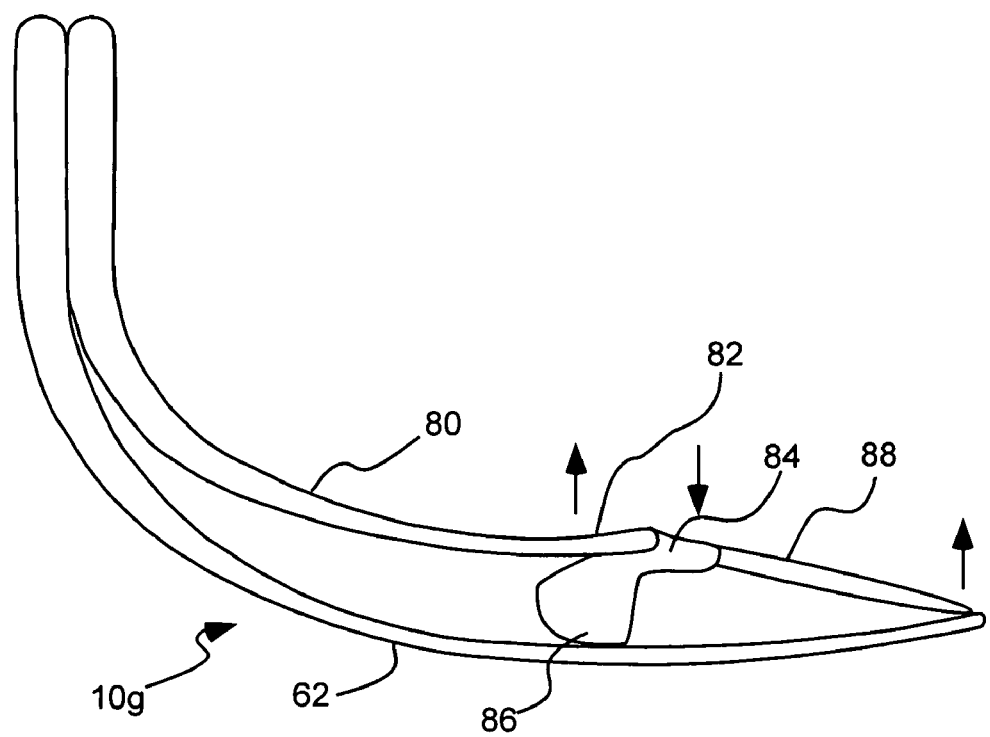
FIG. 10 is a side view of another prosthetic foot in accordance with the present invention.

Referring to FIG. 10, another prosthetic foot 10g includes a cantilever-spring defining a resistance arm 80 with a deflection section 82. In this aspect, the means for variably inter-coupling the cantilever-springs can include a cam 84 pivotally coupled to the deflection section of the resistance arm. The cam 84 can have a lobe 86 which extends to directly engage the foot member 62. A lever arm 88 can be fixedly attached to the cam 84 and can engage the foot member. As the foot member 62 deflects, it displaces the lever arm 88. As the lever arm 88 displaces, the cam 84 pivots. As the cam 84 pivots, it forces the foot member 62 and resistance arm 80 apart.

Figure 11:
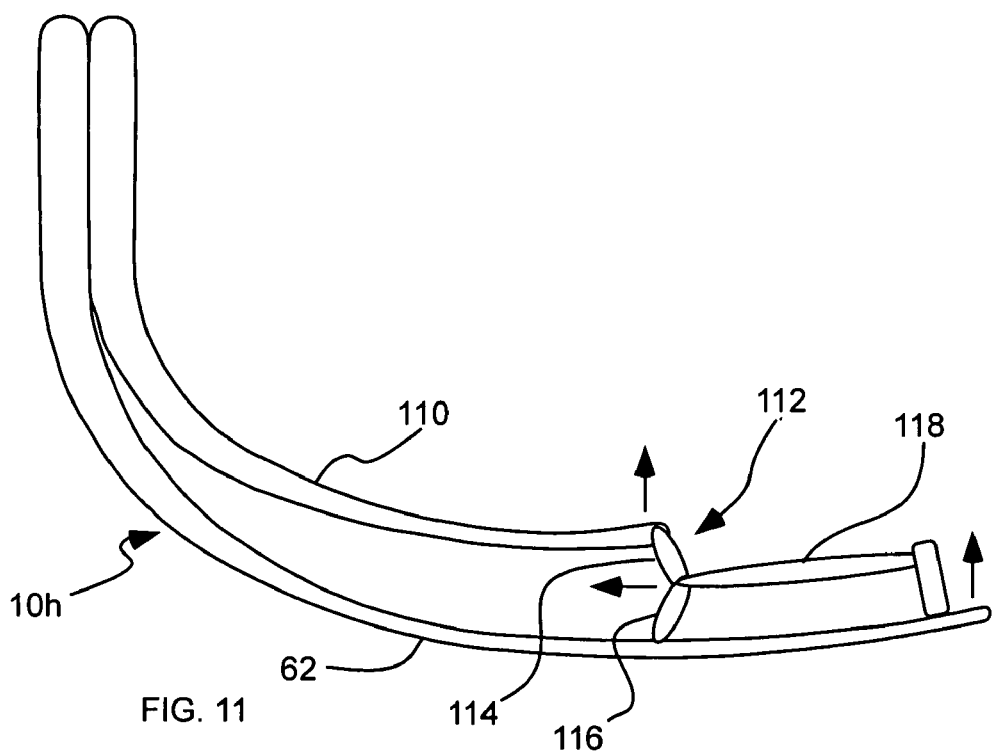
FIG. 11 is a side view of another prosthetic foot in accordance with the present invention.

Referring to FIG. 11, another prosthetic foot 10h includes a linkage. A cantilever-spring defines a resistance arm 110. The means for variably inter-coupling the cantilever-springs can include a linkage 112 coupled between the foot member 62 and the resistance arm 110. The linkage can include a pair of links 114 and 116 coupled in series between the foot member 62 and the resistance arm 110. The links 114 and 116 can have an extended length that is greater than a distance between the foot member 62 and the resistance arm 110 (that is, the links must be collapsed upon one another in order to fit between the foot member and resistance arm). An armature 118 can be coupled to the foot member 62 and can engage the linkage 112. As the foot member 62 deflects, it displaces the armature 118. As the armature 118 displaces, it extends the pair of links from a shorter length to a greater length. As the pair of links extend, they force the foot member and the resistance arm apart.

Figure 12:
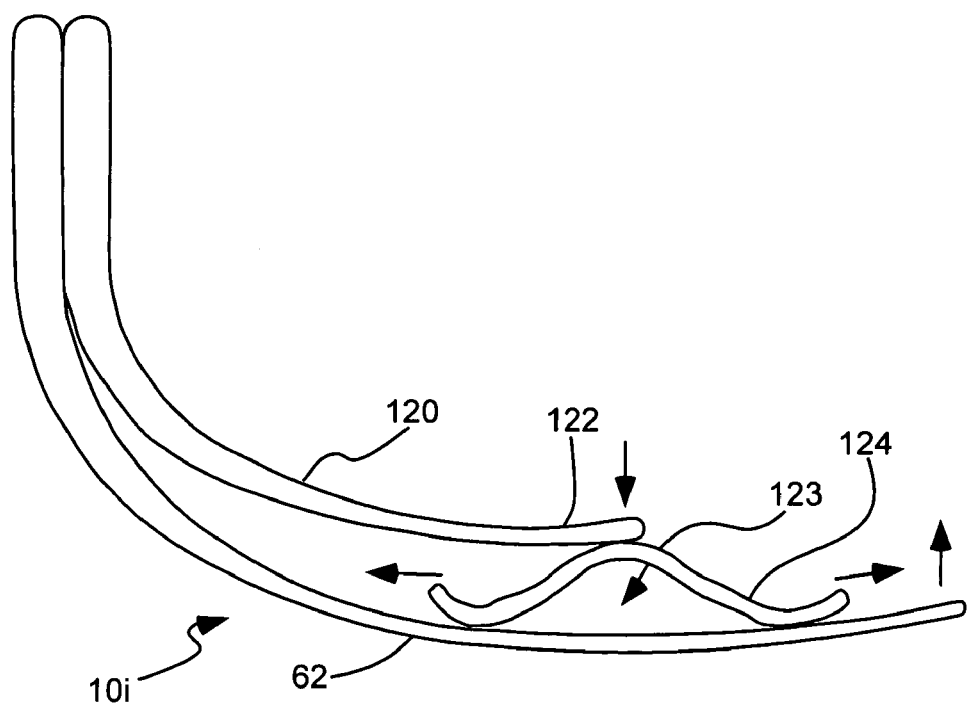
FIG. 12 is a side view of another prosthetic foot in accordance with the present invention.

Referring to FIG. 12, another prosthetic foot 10i includes a leaf spring. A cantilever-spring defines a resistance arm 120 with a deflection section 122 defining a gap 123 between the foot member 62 and the deflection section 122 of the resistance arm. The means for variably inter-coupling the cantilever-springs can include a leaf-spring 124 disposed in the gap 123 and engaging the foot member and the resistance arm. The leaf spring can be compressible and can have an extendable length during compression. As the foot member 62 deflects, it compresses the leaf-spring 124 in the gap 123. As the leaf-spring compresses, its deflects the resistance arm 120, and its length extends to vary the force applied from the foot member to the resistance arm.

As discussed above in connection with FIG. 1c, the prosthetic foot is configured to store a greater amount of energy than generally storable with a linear spring. Thus, the means for variably inter-coupling the cantilever-springs can further include means for inter-coupling the cantilever-springs such that one of the cantilever-springs initially applies a greater force to the foot member. An example of such means includes the lever arm and the resistance arm initially coupled at different distances from the pivot. In another aspect of the invention, the means for variably inter-coupling the cantilever-springs further includes means for inter-coupling the cantilever-springs such that the cantilever-springs together have a non-linear force and deflection relationship.

Referring to FIGS. 13a and 13b, another prosthetic foot 10j is shown that is similar in many respects to those described above. The prosthetic foot 10j can include a plurality of cantilever-springs, including an elongated continuous cantilever-spring 12j defining a unitary foot member. The cantilever-spring 12j or foot member includes an attachment section 14j that is couplable to a stump or socket (not shown) of an amputee. The cantilever-spring 12j or foot member can extend from the attachment section 14j to a toe section 16j at a toe location of a natural foot. The foot member can form a substantial j-shape. As described above, a cam 20 can be pivotally coupled to the cantilever-spring 12j at a pivot. The prosthetic foot 10j can include a pair of cams disposed on opposite lateral sides of the cantilever-spring.

Another of the plurality of cantilever-springs can form a resistance arm 24j with an attachment section couplable to the stump of the amputee and extendable to a displaceable section 26j. The resistance arm 24j can form an arc with a substantial u-shape. The displaceable section 26j can engage the cam 20, as discussed above via cable(s) 38.

A lever arm 28j can be attached to the cantilever-spring 12j or foot member. In addition, the lever arm 28j can extend to an upper end or displaceable section that can engage the cam 20, as discussed above via cable(s) 36. Thus, the cam operatively inter-couples the cantilever-spring 12j and the resistance arm 24j to elastically deform the resistance arm 24j along with the cantilever-spring 12j to collectively store more energy than the cantilever-spring alone.

It is to be understood that the above-referenced arrangements are illustrative of the application for the principles of the present invention. It will be apparent to those of ordinary skill in the art that numerous modifications can be made without departing from the principles and concepts of the invention as set forth in the claims.

What is claimed is:

1. A prosthetic foot device, comprising:
   an elongated continuous cantilever-spring, extending from an attachment section coupleable to a stump of an amputee to a toe section at a toe location of a natural foot;
   the cantilever-spring being elastically deformable under a load to store energy as the amputee steps onto the cantilever-spring and to release energy as the amputee steps off of the cantilever-spring;
   a cam, pivotally coupled to the cantilever-spring at a pivot;
   a resistance arm, coupleable to the stump of the amputee, and extending to a displaceable section engaging the cam;
   a lever arm, attached to the cantilever-spring, and engaging the cam; and
   the cam operatively inter-coupling the cantilever-spring and the resistance arm to elastically deform the resistance arm along with the cantilever-spring to collectively store more energy than the cantilever-spring alone.

2. The device of claim 1, wherein:
   the resistance arm and the lever arm initially engage the cam at different distances from the pivot, with the lever arm engaging the cam at a closer distance to the pivot and the resistance arm engaging the cam at a further distance to the pivot; and the resistance arm and the lever arm engage the cam at varying distances from the pivot as the cam pivots, with the lever arm engaging the cam at a distance varying from closer to further as the cam pivots and with the resistance arm engaging the cam at a distance varying from further to closer as the cam pivots.

3. The device of claim 1, wherein the lever arm and the resistance arm are disposed on opposite sides of the cantilever-spring.

4. The device of claim 3, wherein the cam includes a pair of lobes disposed at different circumferential positions with respect to the pivot.

5. The device of claim 3, wherein the cam includes a dual cam with a pair of lobes disposed at different circumferential positions with respect to the pivot.

6. The device of claim 1, wherein the cam includes a pair of cams fixed to one another and pivotal together, the pair of cams being oriented at different orientations with respect to one another.

7. The device of claim 1, wherein the cam has a pair of tracks extending around at least a portion of a perimeter of the cam, the tracks extending at different circumferential distances from the pivot.

8. The device of claim 1, wherein the cantilever-spring is curvilinear and extends continuously from the attachment section, through an ankle section and an arch section, to the toe section.

9. A prosthetic foot device, comprising:
a plurality of cantilever-springs, being capable of elastic deformation under a load to store and release energy;
a cam, pivotal with respect to the cantilever-springs;
the cam operatively inter-coupling the cantilever-springs such that the cantilever-springs store more energy together than alone;
one of the cantilever-springs having an attachment section coupleable to a stump of an amputee and defining a unitary foot member extending continuously from the attachment section to a toe section at a toe location of a natural foot; and
wherein the foot member is curvilinear and extends continuously from the attachment section, through an ankle section and an arch section, to the toe section.

10. The device of claim 9, further comprising a lever arm, attached to the foot member, and coupleable to the cam.

11. The device of claim 10, wherein another of the cantilever-springs defines a resistance arm; and wherein the resistance arm and the lever arm are disposed on opposite sides of the foot member.

12. The device of claim 9, wherein the cam includes a pair of cams fixed to one another and pivotal together, the pair of cams being oriented at different orientations with respect to one another.

13. The device of claim 9, wherein the cam has a pair of tracks extending around at least a portion of a perimeter of the cam, the tracks extending at different circumferential distances from the pivot.

14. A prosthetic foot device, comprising:
a plurality of cantilever-springs, each having an attachment section coupleable to a stump of an amputee, the cantilever-springs being capable of elastic deformation under a load to store and release energy;
one of the cantilever-springs defining a unitary foot member extending continuously from the attachment section to a toe section at a toe location of a natural foot;
another of the cantilever-springs defining a resistance arm with a deflection section; and
means for variably inter-coupling the cantilever-springs so that one of the cantilever-springs applies a varying resistance force to the foot member that varies as the foot member deflects; including:
a cam, pivotally coupled to the deflection section of the resistance arm;
a lever arm, coupled to the cam and engaging the foot member; and
a cable, coupled to the cam and engaging the foot member; and wherein
the cantilever-springs are inter-coupled such that the foot member displaces the lever arm as the foot member deflects; the cam pivots as the lever arm displaces; and the cable pulls the foot member and resistance arm together as the cam pivots.

15. A prosthetic foot device, comprising:
a plurality of cantilever-springs, each having an attachment section coupleable to a stump of an amputee, the cantilever-springs being capable of elastic deformation under a load to store and release energy;
one of the cantilever-springs defining a unitary foot member extending continuously from the attachment section to a toe section at a toe location of a natural foot;
another of the cantilever-springs defining a resistance arm with a deflection section; and
means for variably inter-coupling the cantilever-springs so that one of the cantilever-springs applies a varying resistance force to the foot member that varies as the foot member deflects, including:
a cam, pivotally coupled to the deflection section of the resistance arm, the cam having a lobe extending to engage the foot member;
a lever arm, coupled to the cam and engaging the foot member; and wherein
the cantilever-springs are inter-coupled such that the foot member displaces the lever arm as the foot member deflects; the cam pivots as the lever arm displaces; and the lobe pushes the foot member and resistance arm apart as the cam pivots.

16. A prosthetic foot device, comprising:
a plurality of cantilever-springs, each having an attachment section coupleable to a stump of an amputee, the cantilever-springs being capable of elastic deformation under a load to store and release energy;
one of the cantilever-springs defining a unitary foot member extending continuously from the attachment section to a toe section at a toe location of a natural foot;
a mounting arm having an attachment section coupleable to the stump of the amputee;
another of the cantilever-springs defining a resistance arm with a deflection section;
means for variably inter-coupling the cantilever-springs so that one of the cantilever-springs applies a varying resistance force to the foot member that varies as the foot member deflects, including:
a cam, pivotally coupled to the mounting arm;
a lever arm, coupled to the cam and engaging the foot member; and
a cable, coupled to the cam and engaging the resistance arm; and wherein
cantilever-springs are inter-coupled such that the foot member displaces the lever arm as the foot member deflects; the cam pivots as the lever arm displaces; and the cable pulls the resistance arm as the cam pivots.

17. A prosthetic foot device, comprising:
a plurality of cantilever-springs, each having an attachment section coupleable to a stump of an amputee, the cantilever-springs being capable of elastic deformation under a load to store and release energy;

one of the cantilever-springs defining a unitary foot member extending continuously from the attachment section to a toe section at a toe location of a natural foot;

another of the cantilever-springs defining a resistance arm; and means for variably inter-coupling the cantilever-springs so that one of the cantilever-springs applies a varying resistance force to the foot member that varies as the foot member deflects, including a linkage, coupled between the foot member and the resistance arm, the linkage including:

a pair of links, coupled in series between the foot member and the resistance arm, the links having an extended length greater than a distance between the foot member and the resistance arm; and an armature, coupled to the foot member and engaging the linkage; and wherein the cantilever-springs are inter-coupled such that the foot member displaces the armature as the foot member deflects; the armature extends the pair of links from a shorter length to a greater length as the armature displaces; and the pair of links pushes against the resistance arm as the pair of links extend.

18. A prosthetic foot device, comprising:

a plurality of cantilever-springs, each having an attachment section coupleable to a stump of an amputee, the cantilever-springs being capable of elastic deformation under a load to store and release energy;

one of the cantilever-springs defining a unitary foot member extending continuously from the attachment section to a toe section at a toe location of a natural foot;

another of the cantilever-springs defining a resistance arm with a deflection section defining a gap between the foot member and the deflection section of the resistance arm; and means for variably inter-coupling the cantilever-springs so that one of the cantilever-springs applies a varying resistance force to the foot member that varies as the foot member deflects, including:

a leaf-spring, disposed in the gap and engaging the foot member and the resistance arm, the leaf spring being compressible and having an extendable length during compression; and wherein the cantilever-springs are inter-coupled such that the foot member compresses the leaf spring as the foot member deflects; and the leaf spring extends in length during compression.

\* \* \* \* \*